US008834507B2

(12) United States Patent  
Mire et al.

(10) Patent No.: US 8,834,507 B2
(45) Date of Patent: Sep. 16, 2014

(54) DILATION INSTRUMENTS AND METHODS

(75) Inventors: David A. Mire, Cordova, TN (US); Kelli N. Sebastian, Arlington, TN (US); John A. Elliott, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 640 days.

(21) Appl. No.: 13/109,028

(22) Filed: May 17, 2011

(65) Prior Publication Data

US 2012/0296359 A1 Nov. 22, 2012

(51) Int. Cl.
*A61M 29/00* (2006.01)
*A61B 17/34* (2006.01)
*A61B 17/32* (2006.01)
*A61B 19/00* (2006.01)
*A61B 17/00* (2006.01)

(52) U.S. Cl.
CPC . *A61B 17/3421* (2013.01); *A61B 2017/320004* (2013.01); *A61B 2017/320008* (2013.01); *A61B 2019/462* (2013.01); *A61B 2017/00261* (2013.01); *A61B 2017/320044* (2013.01)
USPC ...................................................... 606/191

(58) Field of Classification Search
CPC ............... A61B 17/3421; A61B 17/56; A61B 2017/00261; A61B 17/320004; A61B 17/320008; A61B 17/320044; A61B 17/462
USPC ........ 606/1, 67, 190, 191, 329, 160; 600/566, 600/567, 570
See application file for complete search history.

(56) References Cited

U.S. PATENT DOCUMENTS

| D247,512 | S | * | 3/1978 | Sandler ..................... 606/191 |
| 4,895,564 | A | | 1/1990 | Farrell |
| 5,171,279 | A | | 12/1992 | Mathews |
| 5,201,735 | A | * | 4/1993 | Chapman et al. ............... 606/67 |
| 5,275,611 | A | | 1/1994 | Behl |
| 5,312,611 | A | | 5/1994 | Takami et al. |
| 5,472,426 | A | | 12/1995 | Bonati et al. |
| 5,792,044 | A | | 8/1998 | Foley et al. |
| 6,159,179 | A | | 12/2000 | Simonson |
| 6,520,953 | B1 | * | 2/2003 | Schultz ............................ 606/1 |
| 6,743,207 | B2 | | 6/2004 | Elbert et al. |
| 6,916,330 | B2 | * | 7/2005 | Simonson ..................... 606/191 |
| 7,008,431 | B2 | | 3/2006 | Simonson |
| 7,074,226 | B2 | | 7/2006 | Roehm, III et al. |
| 7,166,088 | B2 | | 1/2007 | Heuser |
| 7,427,264 | B2 | | 9/2008 | Nowitzke et al. |
| 7,618,088 | B2 | | 11/2009 | Bauer |
| 7,618,431 | B2 | | 11/2009 | Roehm, III et al. |
| 2003/0083688 | A1 | | 5/2003 | Simonson |
| 2004/0059339 | A1 | | 3/2004 | Roehm, III et al. |

(Continued)

FOREIGN PATENT DOCUMENTS

WO WO 2008/024883 2/2008
WO WO 2009/046414 4/2009

*Primary Examiner* — Julian W Woo
(74) *Attorney, Agent, or Firm* — Sorell Lenna & Schmidt LLP

(57) ABSTRACT

Devices, systems and methods for dilating tissue of a patient during a minimally invasive surgical procedure is disclosed. A surgical dilation system includes a dilator having an elongated, non-cannulated cylindrical body extending between a first end and an opposite second end. The first end includes a first beveled configuration and the second end includes a second, different beveled configuration. The beveled ends can include surface features to provide tissue removal and to enhance engagement with bony tissue.

20 Claims, 6 Drawing Sheets

(56) References Cited

U.S. PATENT DOCUMENTS

| | | |
|---|---|---|
| 2004/0147950 A1 | 7/2004 | Mueller, Jr. et al. |
| 2005/0004593 A1 | 1/2005 | Simonson |
| 2005/0080443 A1 | 4/2005 | Fallin et al. |
| 2005/0137607 A1 | 6/2005 | Assell et al. |
| 2005/0216002 A1 | 9/2005 | Simonson |
| 2005/0234497 A1 | 10/2005 | Hung et al. |
| 2006/0004398 A1 | 1/2006 | Binder, Jr. et al. |
| 2006/0004401 A1 | 1/2006 | Abernathie et al. |
| 2006/0030861 A1 | 2/2006 | Simonson et al. |
| 2006/0030872 A1 | 2/2006 | Culbert et al. |
| 2006/0200139 A1 | 9/2006 | Michelson |
| 2006/0217664 A1 | 9/2006 | Hattler |
| 2006/0229656 A1 | 10/2006 | McDonnell |
| 2006/0247651 A1 | 11/2006 | Roehm, III et al. |
| 2006/0287574 A1 | 12/2006 | Chin |
| 2007/0100366 A1 | 5/2007 | Dziedzic et al. |
| 2007/0142778 A1 | 6/2007 | Elbert et al. |
| 2007/0161956 A1 | 7/2007 | Heuser |
| 2007/0198044 A1* | 8/2007 | Lupton et al. .................. 606/191 |
| 2008/0051821 A1 | 2/2008 | Gephart |
| 2008/0177259 A1 | 7/2008 | Wu |
| 2008/0287981 A1 | 11/2008 | Culbert et al. |
| 2008/0294171 A1 | 11/2008 | Boehm, Jr. |
| 2009/0125030 A1 | 5/2009 | Tebbe et al. |
| 2009/0147857 A1 | 6/2009 | Park et al. |
| 2009/0270902 A1 | 10/2009 | Assell et al. |
| 2009/0275802 A1 | 11/2009 | Hawkes et al. |
| 2010/0114147 A1 | 5/2010 | Biyani |
| 2010/0160947 A1 | 6/2010 | Akyuz et al. |
| 2010/0222824 A1 | 9/2010 | Simonson |

* cited by examiner

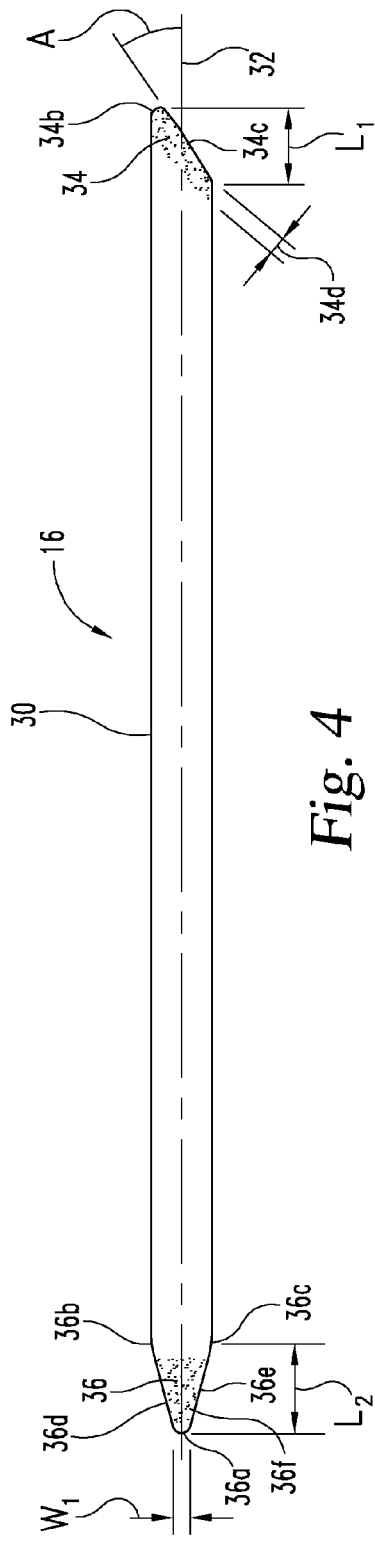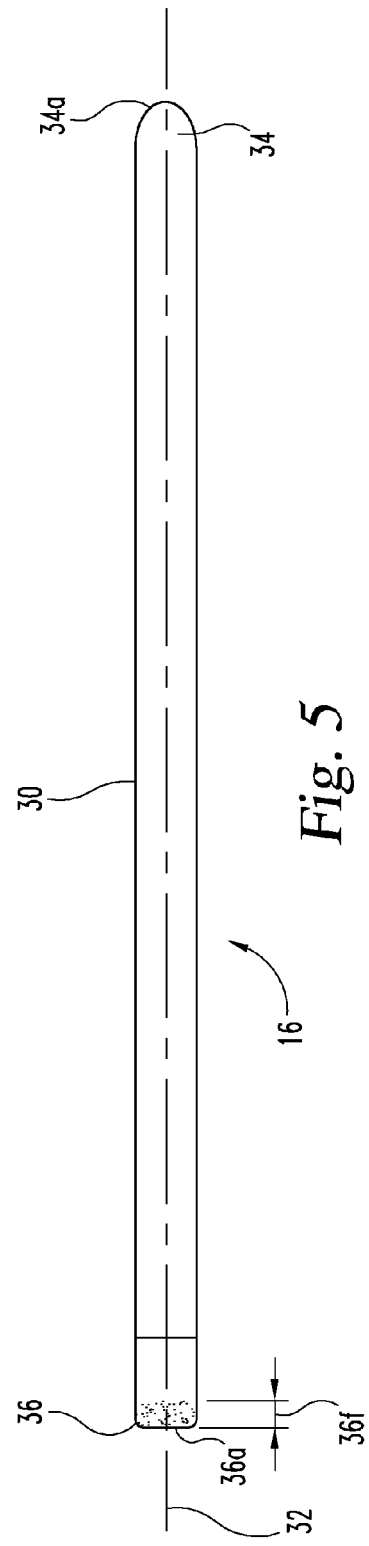

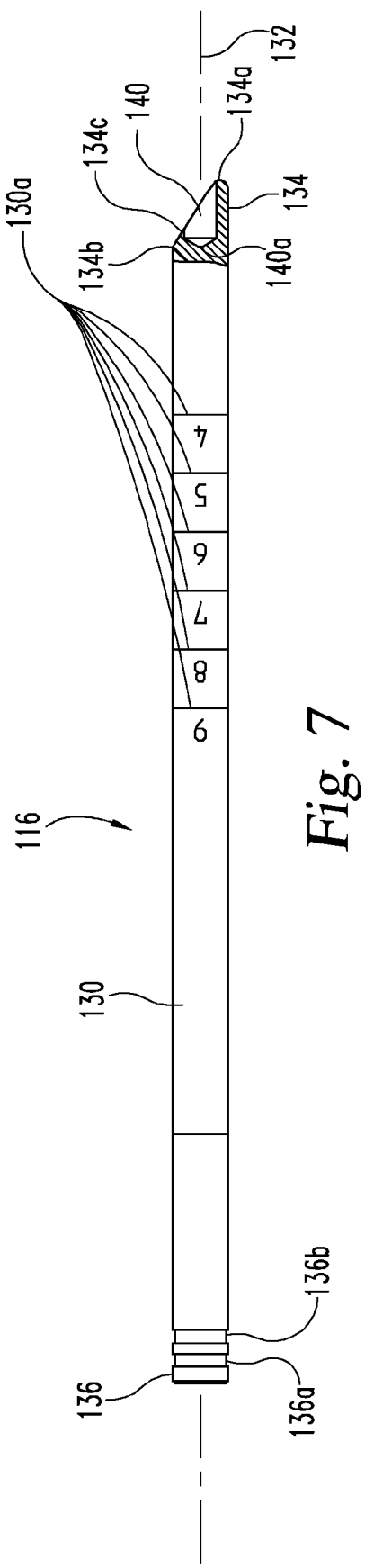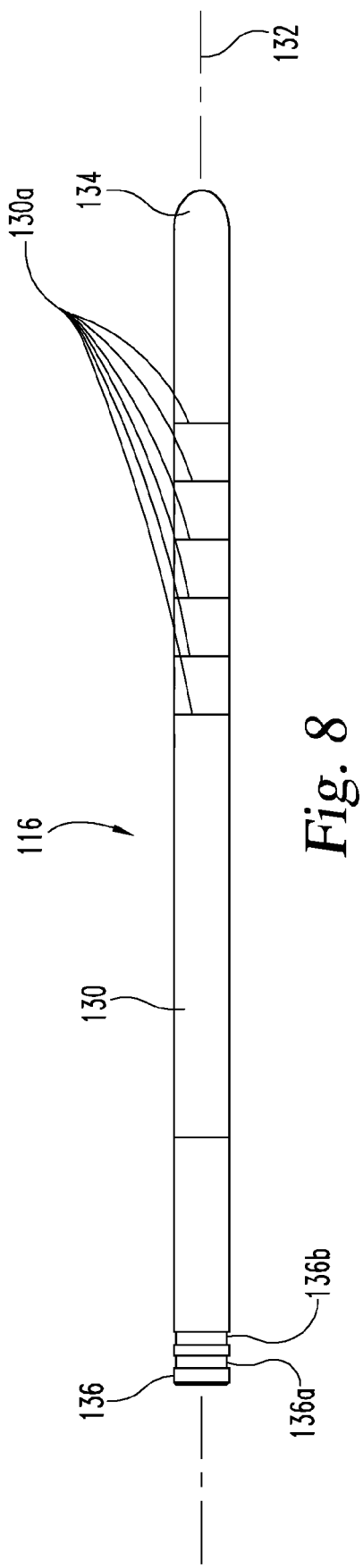

DILATION INSTRUMENTS AND METHODS

FIELD OF THE INVENTION

The present invention relates generally to instruments and methods for performing surgeries and more particularly, to devices, methods and systems for performing minimally invasive spinal surgeries.

BACKGROUND

Traditional surgical procedures for pathologies located deep within the body can cause significant trauma to the intervening tissues. These open procedures often require a long incision, extensive muscle stripping, prolonged retraction of tissues, denervation and devascularization of tissue. Most of these surgeries require a recovery room time of several hours and several weeks of post-operative recovery time due to the use of general anesthesia and the destruction of tissue during the surgical procedure. In some cases, these invasive procedures lead to permanent scarring and pain that can be more severe than the pain leading to the surgical intervention.

Minimally invasive alternatives such as arthroscopic techniques reduce pain, post-operative recovery time and the destruction of healthy tissue. Orthopedic surgical patients have particularly benefitted from minimally invasive surgical techniques. The site of pathology is accessed through portals rather than through a significant incision thus preserving the integrity of the intervening tissues. In some instances, these minimally invasive techniques require only local anesthesia. The avoidance of general anesthesia reduces post-operative recovery time and the risk of complications.

Minimally invasive surgical techniques are particularly desirable for spinal and neurosurgical applications because of the need for access to locations deep within the body and the danger of damage to vital intervening tissues. For example, a common open procedure for disc herniation, laminectomy followed by discectomy requires stripping or dissection of the major muscles of the back to expose the spine. In a posterior approach, tissue including spinal nerves and blood vessels around the dural sac, ligaments and muscle must be retracted to clear a channel from the skin to the disc. These procedures normally take at least one-two hours to perform under general anesthesia and require post-operative recovery periods of at least several weeks. In addition to the long recovery time, the destruction of tissue is a major disadvantage of open spinal procedures. This aspect of open procedures is even more invasive when the discectomy is accompanied by fusion of the adjacent vertebrae. Many patients are reluctant to seek surgery as a solution to pain caused by herniated discs and other spinal conditions because of the severe pain sometimes associated with the muscle dissection.

In order to reduce the post-operative recovery time and pain associated with spinal and other procedures, micro-surgical techniques have been developed. The objective of any minimally invasive procedure is to accomplish the same clinical objectives as the traditional, open surgery while minimizing soft tissue retraction. Existing sequential dilation processes consist of inserting a guide wire and multiple increasing diameter dilators until the correct diameter is achieved. A retractor is then placed over the dilators and the dilators are then removed. The retractor is left in place with the surrounding muscle and tissue having been dilated out of the working space.

It is beneficial to reduce the steps associated with dilation of the access portal to minimize the time of surgery and simplify the surgical procedure.

SUMMARY

According to one aspect a surgical dilator is disclosed that is configured to dilate an incision and tissue in a patient. The surgical dilator includes an elongated cylindrical body with a beveled configuration on each end of the dilator. The beveled configurations differ from one another so that the surgeon can select therefrom the most desirable configuration use in the procedure. In one form, the dilator is non-cannulated, and the beveled first and second ends allow elimination of the use of guide wires and/or needles to initiate formation of the pathway to the surgical location in the patient. In another form, the dilator includes a cavity extending into the end surface of the beveled end. In yet another form, the beveled end or ends includes surface features that enhance the engagement of the dilator to bone. The surface features can improve traction of the dilator with the bone, provide for bone and tissue removal, and provide secure docking of the dilator on the bone.

The surgical dilator may be used during surgery as an initial dilator that is guided through the skin and/or tissue to position the beveled end against bone. The initial dilator defines a pathway to the bone. One or more additional dilators can then be placed around the initial dilator to increase the size of the pathway. Once the desired pathway size is achieved, a retractor can be placed around or adjacent to the last inserted dilator to maintain the pathway. The dilators can then be removed from the pathway.

Related features, aspects, embodiments, objects and advantages of the present invention will be apparent from the following description.

BRIEF DESCRIPTION OF THE DRAWINGS

FIG. 4 is a side view of the dilator of FIG. 3.

FIG. 5 is another side view of the dilator of FIG. 3.

FIG. 7 is a side view of the dilator of FIG. 6 showing the distal end of the dilator in section.

FIG. 8 is another side view of the dilator of FIG. 6.

DESCRIPTION OF THE ILLUSTRATED EMBODIMENTS

Figure 1:
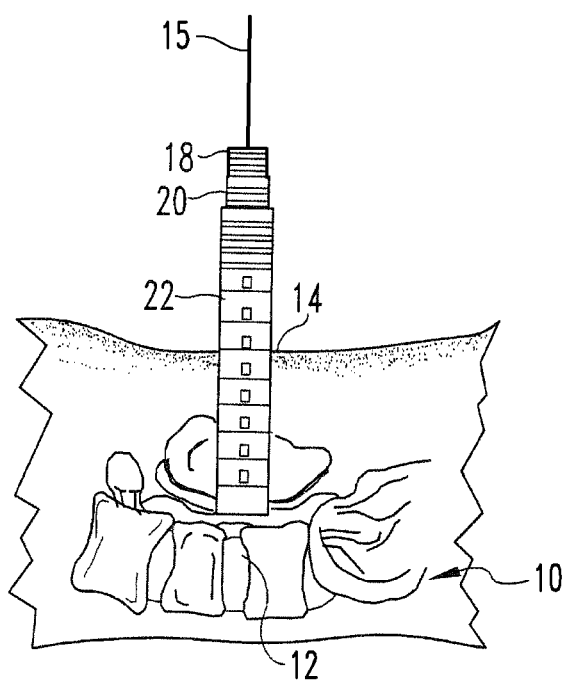
FIG. 1 illustrates a prior art dilation system that comprises a plurality of dilators each having a larger outside diameter than the other inserted into a patient.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Referring to FIG. 1, a system, device and method for use in connection with a posterior approach to the lumbar portion of the spinal column is shown and will be generally discussed. Although a posterior lumbar approach is described herein, it should be readily appreciated that the principles of the present invention can be applied to many other types of minimally invasive surgical procedures as well. As such, the fact that a posterior lumbar approach to the spinal column is described in connection herewith should not be construed in any way as a limitation of the present invention unless expressly set forth in the claims.

A discectomy procedure typically begins with a surgeon precisely locating a herniated disc with a very small needle (not shown) that is inserted to form an access pathway 14 through the muscles of the back down to an area of the spine 10 where spinal disc fragments 12 are located. The correct position of the needle is typically confirmed using a fluoroscope, although the use of any imaging technology is contemplated herein. Once this is accomplished, a small incision is made at the puncture site. Typically, the incision length will match the outside diameter of the largest tubular dilator (e.g. —21 millimeters). A guide wire 15 may then be inserted into the incision and placed in the proper position in relation to the disc fragments 12 that are to be removed. Alternatively, the needle can be cannulated and used to guide the guide wire 15 to the target location. The cannulated needle is then removed while the guide wire remains in place along pathway 14 to guide the remaining dilators 18, 20, 22 that are of increasing diameter and positioned sequentially one over the other to expand the size of pathway 14. Again, a fluoroscope may be used to confirm that the guide wire and dilators are placed in the proper position.

Figure 2:
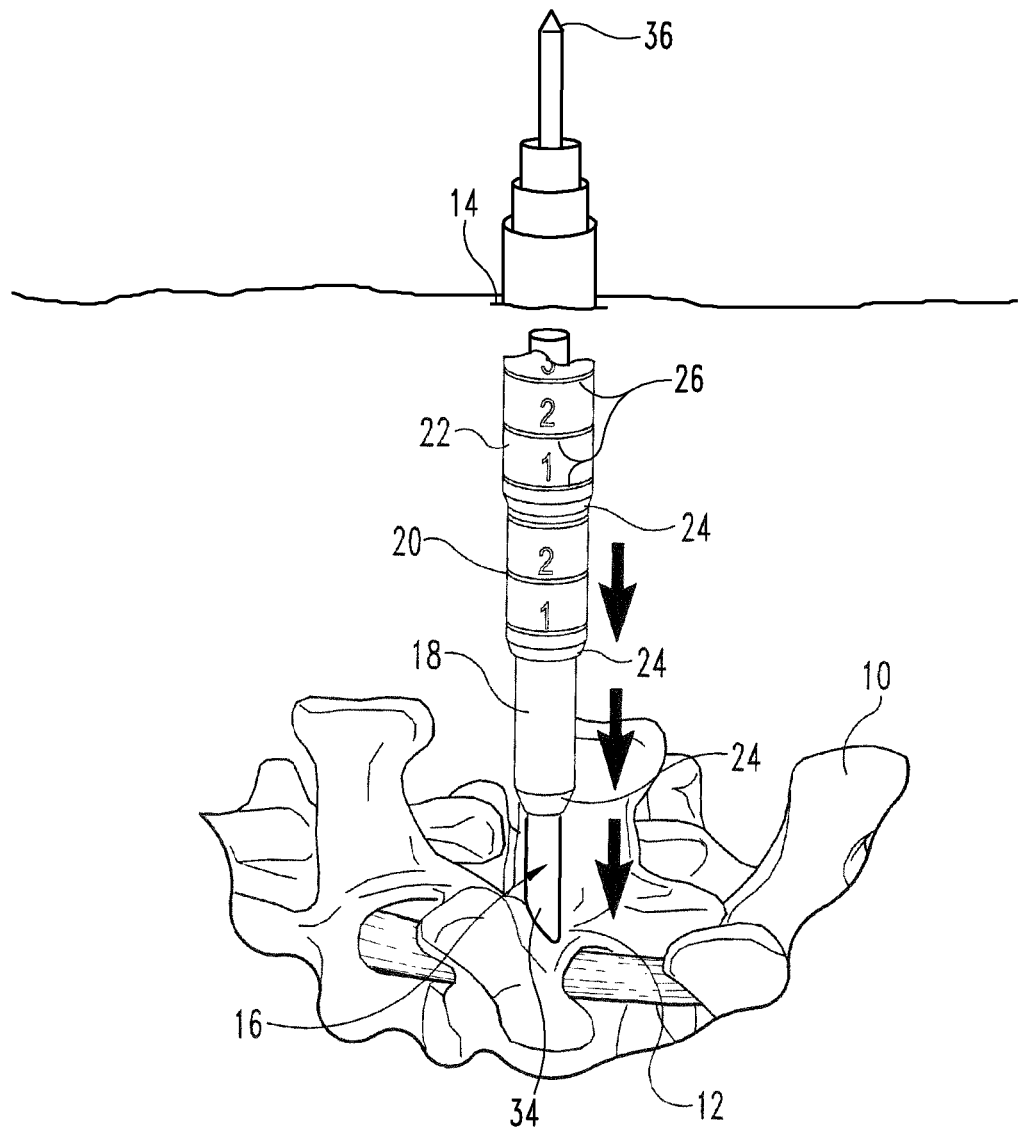
FIG. 2 illustrates a dilation system inserted into a patient using an initial dilator to form the pathway to the surgical site.

Referring to FIG. 2, an initial, non-cannulated dilator 16 is positioned through skin S and intervening tissue between spine 10 and skin S to define pathway 14. The first dilator 16 may be used to palpate the incision in both the sagittal and coronal planes. In addition, first dilator 16 is docked to bone of spine 10 to provide a platform for guiding additional dilators to increase the size of pathway 14. Once the dilator 16 is placed in the proper position, a second cannulated soft tissue dilator 18 is inserted over the initial dilator 16 and through the pathway 14 to a desired depth. At this point, dilator 16 can be removed from within the second dilator 18, although it typically remains in position to facilitate guiding of additional dilators. Next, third, and fourth cannulated soft tissue dilators 20 and 22 are sequentially placed over one another and inserted through the pathway 14 to the desired depth to increase the size of pathway 14 in an incremental manner. In the illustrated form, a distal end 24 of each cannulated soft tissue dilator has a tapered or beveled leading end configuration to help facilitate insertion of the dilator through the skin and intervening muscle and tissue. Further, in other forms, one or more of the cannulated soft tissue dilators 18, 20, 22 disclosed herein may include depth indicators or markings 26 on an outside surface to help inform the surgeon as to what depth the cannulated soft tissue dilators have been inserted into the patient.

In one illustrative form, the first cannulated soft tissue dilator 18 has a maximum outside dimension of 14 millimeters, the second cannulated soft tissue dilator 20 has a maximum outside dimension of 18 millimeters, and the third cannulated soft tissue dilator 22 has a maximum outside dimension of 20 millimeters. In the illustrated embodiment, each dilator includes a circular cross-section and the maximum dimension is a diameter. In other embodiments, the dilators include non-circular cross-sections, such as oval, elliptical, or racetrack shaped cross-sections. Although three cannulated soft tissue dilators 18, 20, 22 are utilized in the illustrated form, it should be appreciated that any number of cannulated soft tissue dilators could be used in other forms of the present invention. Further, the outside diameters of the cannulated soft tissue dilators could also vary in size in other forms of the present invention and the illustrative diameters set forth above should not be construed as a limitation of the present invention. The lumen or hollow interior portions of each cannulated soft tissue dilator is sized to fit or slide over the outside diameter of next smaller dilators. In one specific embodiment, the increment in size of the outside dimension or diameter from one dilator to the next larger dilator ranges from 2 to 4 millimeters, but other increments are also contemplated. It is also contemplated that fewer than three cannulated tissue dilators or four or more cannulated tissue dilators may be employed depending on the desired size of pathway 14.

Figure 3:
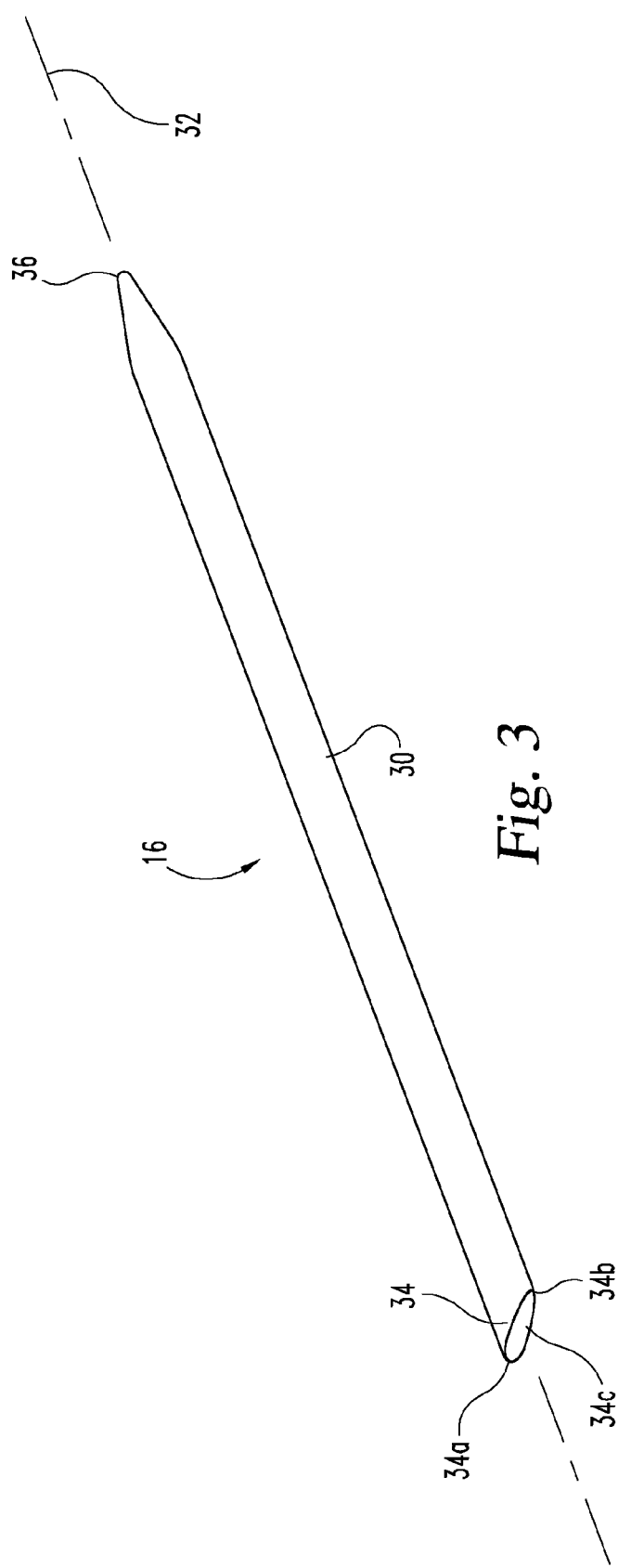
FIG. 3 is a perspective view of the initial dilator of the dilation system of FIG. 2.

Referring collectively to FIGS. 3-5, dilator 16 is shown. Dilator 16 includes an elongated, solid cylindrical body 30 extending on a center defined by longitudinal axis 32 between a first end 34 and an opposite second end 36. In one specific embodiment, dilator 16 defines an overall length between first and second end 34, 36. In one specific embodiment, the overall length is about 230 millimeters. However, other embodiments contemplate other lengths so long as when one of first and second ends 34, 36 is positioned in contact with bony structure in the patient the other of the first and second ends 34, 36 is located outside the skin S of the patient to facilitate positioning of the additional dilators around dilator 16. In addition, body 30 includes a circular cross-section orthogonal to longitudinal axis 32 with a diameter of about 9.5 millimeters. Accordingly, in one specific embodiment, the overall length of body 30 between ends 34, 36 is about 20 times greater than its maximum cross-sectional dimension. However, other embodiments contemplate other dimensions and cross-sectional shapes for dilator 16, including oval, elliptical, racetrack shapes, for example.

First end 34 includes a single beveled configuration in which an end-most tip 34a is formed on one side of body 30 in offset relation to longitudinal axis 32. The initiation of the beveled configuration begins at a transition 34b of body 30 at a side of body 30 located opposite tip 34a. The end surface 34c extends from transition 34b to end-most tip 34a and forms an angle A with longitudinal axis 32. In one embodiment, angle A ranges from about 10 degrees to 60 degrees. In a further embodiment, angle A ranges from 30 to 35 degrees. In one specific embodiment, angle A is about 32 degrees. End-most tip 34a is defined by a radius extending from end surface 34c to the adjacent side of body 30. In one specific embodiment, this radius is about 1.5 millimeters. In addition, first end 34 defines a length L1 from end-most tip 34a to transition 34b. Length L1 is about 11.5 millimeters in on specific embodiment. End 34 provides a blunt, non-cutting configuration that separates the muscle and intervening tissue as dilator 16 is advanced to the surgical site.

Second end 36 includes a double-beveled configuration in which an end-most tip 36a is located on longitudinal axis 32. The initiation of the double-beveled configuration begins one each of opposite sides of body 30 at transitions 36b, 36c. End surfaces 36d, 36e extend from end-most tip 36a to transitions 36b, 36c, respectively, in an oblique orientation to longitudinal axis 32. Second end 36 defines a length L2 from end-most tip 36a to transitions 36b, 36c. Length L1 is about 15 millimeters in one specific embodiment. In addition, end-most tip 36a defines a width W1. In one specific embodiment, width W1 is about 2.5 millimeters. End 36 provides a blunt, non-cutting configuration that separates the muscle and intervening tissue as dilator 16 is advanced to the surgical site.

Ends 34, 36 can also be provided with engagement features on their outer surfaces that enhance traction of the dilator 16 to bone and to assist in removing tissue. For example, first end 34 defines a roughened surface zone 34b extending along the sides of body 30 and end surface 34c. Second end 36 defines a roughened zone 36f that extends from end-most tip 36a along end surfaces 36d, 36e. The roughened surfaces can be formed by knurling, glassbead, blasting, etching, sanding or other suitable means.

Figure 6:
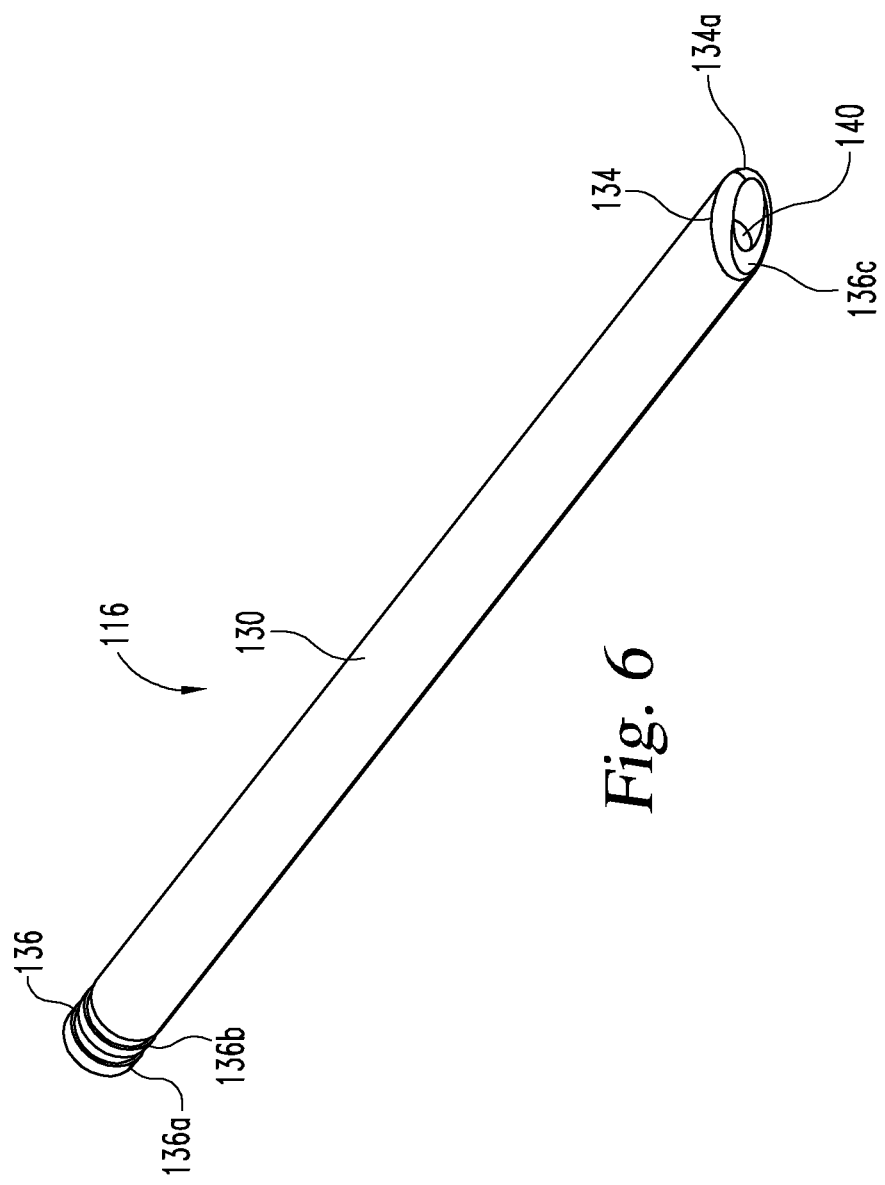
FIG. 6 is a perspective view of another embodiment initial dilator.

Referring now to FIGS. 6-8, there is shown another embodiment dilator 116 that can be positioned to define pathway 14 and to receive one or more additional soft tissue dilators 18, 20, 22 in the same manner as discussed above with respect to dilator 16. Dilator 116 includes an elongated cylindrical body 130 extending on central longitudinal axis 132 between first end 134 and opposite second end 136. First end 134 of dilator 116 is identical to first end 34 of dilator 16 but includes a cavity 140 in end surface 134c between end-most tip 134a and transition 134b. Cavity 140 is centered on longitudinal axis 132 and extends into body 132 to an end 140a located about 10 millimeters from end-most tip 134a. In one specific embodiment, cavity 140 also includes a diameter orthogonal to longitudinal axis 132 that is more than one-half the diameter of body 130. Cavity 140 provides an edge on end surface 134c that can be used to scrape bone and other tissue and to create a surface on the bone for docking end 134 thereon. End 134 provides a blunt, non-cutting configuration that separates the muscle and intervening tissue as dilator 116 is advanced to the surgical site. Although cavity 140 is shown with respect to dilator 116, it is also contemplated that end 34 of dilator 16 can be provided with a cavity 140.

Second end 136 of body 130 does not include a double-beveled configuration like end 36 of dilator 16, although providing end 136 with such a configuration is not precluded. Rather, second end 136 includes a pair of circumferential grooves 136a, 136b extending around body 130 to provide areas which enhance gripping of dilator 116 during insertion, manipulation and removal. In addition, dilator 116 includes a series of depth markings 130a extending around body 130 that provide an indication of the depth to which first end 134 is positioned in the patient. The indicated depth can provide a measure of the required length for the next dilator to position around initial dilator 116. In addition, end 134 can be provided with surface roughening on the sides of body 130 and end surface 134c around cavity 140 such as discussed above with respect to dilator 16.

The dilators disclosed herein can be made from any suitable surgical grade material. In one embodiment, the dilators are made from titanium rather than stainless steel to decrease weight. Other embodiments contemplate other materials, including any suitable plastic, metal, or composite.

Although various embodiments have been described as having particular features and/or combinations of components, other embodiments are possible having a combination of any features and/or components from any of embodiments as discussed above. As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the terms "proximal" and "distal" refer to the direction closer to and away from, respectively, an operator (e.g., surgeon, physician, nurse, technician, etc.) who would insert the medical implant and/or instruments into the patient. For example, the portion of a medical instrument first inserted inside the patient's body would be the distal portion, while the opposite portion of the medical device (e.g., the portion of the medical device closest to the operator) would be the proximal portion.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A surgical dilator, comprising:
an elongated, non-cannulated cylindrical body extending on a straight-line longitudinal axis between a first end and an opposite second end, wherein said body includes a length extending from said first end to said second end and said length is sized so that one of said first and second ends is located outside a skin level of a patient when the other of said first and second ends is positioned in contact with bony structure along the spinal column, wherein said first end includes a cylindrical side surface and a beveled configuration defined by an end surface of said first end, said longitudinal axis extending through said end surface, said beveled configuration forming a first end-most tip offset from said longitudinal axis on one side of said body and said second end includes a double-beveled configuration with a second end-most tip located on said longitudinal axis.

2. The surgical dilator of claim 1, wherein said first end and said second end include surface roughenings on outer surfaces of said body.

3. The surgical dilator of claim 1, wherein said end surface extends obliquely to said longitudinal axis from said first end-most tip to a transition at an opposite second side of said body where said end surface joins said second side of said body.

4. The surgical dilator of claim 3, wherein said body includes a cavity extending on said longitudinal axis into said body from said end surface.

5. The surgical dilator of claim 4, wherein said cavity defines an edge on said end surface for scraping tissue material.

6. The surgical dilator of claim 1, wherein said double-beveled configuration defines a pair of end surfaces extending from said second end-most tip to respective ones of opposite sides of said body, each of said end surfaces extending in an oblique orientation to said longitudinal axis.

7. The surgical dilator of claim 1, wherein said body includes a maximum cross-sectional dimension orthogonal to said longitudinal axis and said length is about 20 times greater than said maximum cross-sectional dimension.

8. The surgical dilator of claim 1, wherein said first end and said second end each define a blunt, non-cutting tip for separating tissue as the body is advanced through tissue.

9. A surgical dilator, comprising:
an elongated, non-cannulated cylindrical body extending on a straight line longitudinal axis between a first end and an opposite second end, wherein said body includes a length extending from said first end to said second end and said length is sized so that one of said first and second ends is located outside a skin level of a patient when the other of said first and second ends is positioned in contact with bony structure along the spinal column, wherein said first end includes a cylindrical side surface and a beveled configuration forming an end-most tip offset from said longitudinal axis to a first side of said body, wherein said first end includes an end surface extending from said end-most tip to a transition at a second side of said body opposite said first side, said body including a cavity extending from said end surface into said body to provide an edge on said end surface for scraping tissue, said longitudinal axis extending through said end surface and a second end surface of said second end.

10. The surgical dilator of claim 9, wherein said cavity is centered on said longitudinal axis.

11. The surgical dilator of claim 9, wherein said second end includes a side surface extending obliquely to said second end surface that defines a double beveled configuration defining a second end-most tip centered on said longitudinal axis.

12. The surgical dilator of claim 11, wherein said side surface extends in an oblique orientation to said longitudinal axis.

13. The surgical dilator of claim 9, wherein said second end includes a plurality of grooves spaced from one another along said longitudinal axis, said grooves each extending circumferentially around said body.

14. The surgical dilator of claim 9, wherein said first end includes surface roughenings on outer surfaces of said body.

15. The surgical dilator of claim 9, wherein said first end defines a blunt, non-cutting tip for separating tissue as the body is advanced through tissue.

16. A method, comprising:
selecting an initial dilator having an elongated, non-cannulated body extending from a first end to an opposite second end along a longitudinal axis, wherein the first end includes a cylindrical side surface and a beveled configuration forming a first end-most tip offset from the longitudinal axis on one side of the body and the second end includes a double-beveled configuration with a second end-most tip located on the longitudinal axis,
selecting one of the first and second ends as the leading insertion end;
positioning the selected leading insertion end into a patient to define a pathway extending from the skin to a bony structure in the patient; and
increasing the size of the pathway by placing at least one additional dilator around the initial dilator.

17. The method of claim 16, further comprising scraping the bony structure with the leading insertion end and then docking the leading insertion end against the bony structure before increasing the size of the pathway.

18. The method of claim 17, wherein the selected leading insertion end includes surface roughenings for securely docking the leading insertion end against the bony structure.

19. The method of claim 17, wherein the leading insertion end includes an end surface extending obliquely to the longitudinal axis and the body defines a cavity extending from the end surface into the body, the cavity defining at least one edge for scraping tissue.

20. The method of claim 16, wherein positioning the selected leading insertion end into the patient is performed without a guide wire.

* * * * *